United States Patent [19]

Fancher

[11] 4,223,028
[45] Sep. 16, 1980

[54] BUTYNYLAMIDE PHOSPHATE AND PHOSPHONATES AND METHOD FOR CONTROLLING INSECTS

[75] Inventor: Llewellyn W. Fancher, Orinda, Calif.

[73] Assignee: Stauffer Chemical Company, Westport, Conn.

[21] Appl. No.: 34,528

[22] Filed: Apr. 30, 1979

[51] Int. Cl.² .................. A01N 9/36; C07F 9/165; C07F 9/32
[52] U.S. Cl. .................................... 424/211; 260/943
[58] Field of Search .................. 260/943; 424/211

[56] References Cited

U.S. PATENT DOCUMENTS

| | | | |
|---|---|---|---|
| 3,004,055 | 10/1961 | Perini et al. | 424/211 |
| 3,057,774 | 10/1962 | Baker et al. | 424/211 |
| 3,752,869 | 8/1973 | Kiehs et al. | 260/943 |
| 3,787,536 | 1/1974 | Bayer et al. | 260/943 |
| 4,152,428 | 5/1979 | Salbeck et al. | 260/943 |

Primary Examiner—Anton H. Sutto
Attorney, Agent, or Firm—Joel G. Ackerman

[57] ABSTRACT

Compounds having the formula

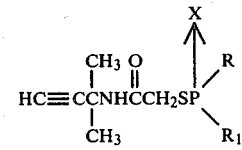

in which
X is selected from the group consisting of sulfur and oxygen;
R is selected from the group consisting of 1–4 carbon alkyl and 1–6 carbon alkoxy; and
$R_1$ is 1–6 carbon alkoxy are useful as insecticides and miticides.

27 Claims, No Drawings

BUTYNYLAMIDE PHOSPHATE AND PHOSPHONATES AND METHOD FOR CONTROLLING INSECTS

This invention relates to novel butynlamide phosphate and phosphonate compounds having the formula $$HC\equiv C-\underset{\underset{CH_3}{|}}{\overset{\overset{CH_3}{|}}{C}}-NH-\overset{\overset{O}{\|}}{C}-CH_2-S-\overset{\overset{X}{\|}}{P}\underset{R_1}{\overset{R}{<}}$$

in which
X is selected from the group consisting of oxygen or sulfur;
R is selected from the group consisting of 1–4 carbon alkyl and 1–6 carbon alkoxy; and
$R_1$ is 1–6 carbon alkoxy.

The compounds of this invention have shown utility as insecticides and miticides.

In one embodiment R is alkyl and the compounds are phosphonates. In another embodiment, R is alkoxy and the compounds are phosphates.

This invention also embodies insecticidal and miticidal compositions of matter comprised of an "insecticidally or miticidally effective amount" of a compound described herein and an inert carrier or diluent. An "insecticidally or miticidally effective amount" is that concentration and application rate necessary to injure or kill a substantial percentage of the treated population.

This invention also relates to the method of controlling or eradicating insects or mites by applying an insecticidally or miticidally effective amount of a compound as defined herein to the insects or mites or their habitat.

Preparation

The compounds typical of this invention are generally prepared by a two-step reaction process. First the intermediate 3-N-chloroacetyl amino-3-methyl-1-butyne is prepared by treatment of a commercially available 1,1-dimethyl propargyl amine with chloroacetic anhydride or chloroacetyl chloride.

The intermediate is reacted with a dithiophosphoric or dithiophosphonic acid ester which is neutralized with a base such as triethylamine in an inert solvent. The solvent can be selected from a variety of such solvents, e.g., tetrahydrofuran, dimethylformamide, etc. The reaction is carried out at or near room temperature to prevent excessive formation of by-products.

An advantageous alternative would be the reaction of 3-N-chloroacetyl amino-3-methyl-1-butyne with the preformed salt of these acids, e.g., sodium or potassium salt.

The following are specific examples of the preparation of compounds typical of this invention. (Compound numbers correspond with those appearing in Table I.)

EXAMPLE 1

(Compound No. 3)

Preparation of 3-N-ethyl,O-isobutylphosphonodithioylacetylamino-3-methyl-1-butyne 3-N-Chloroacetyl amino-3-methyl-1-butyne [3.19 grams (g) or 0.02 mole (M)] was dissolved in 30 milliliters (ml) of tetrahydrofuran and 4.36 g (0.022 M) of ethyl,O-isobutyl dithiophosphonic acid was added with cooling below 15° C. Initially 2.22 g (0.022 M) of triethylamine was added to the mixture with cooling below 25° C., but a few additional drops were required to adjust the pH to 7.5.

The reaction mixture was stirred at ambient temperature overnight. The solvent was then evaporated under reduced pressure. The residue was taken up in 100 ml of methylene chloride. It was washed twice with 100 ml portions of water, dried over magnesium sulfate, filtered, and evaporated under reduced pressure. The 5.89 g (91.7% yield) of product was a light amber colored liquid ($n_D^{30}$ 1.5231). Structure was confirmed by nuclear magnetic resonance (NMR).

EXAMPLE 2

(Compound No. 5)

Preparation of 3-N-O,O-diethylphosphorodithioylacetylamino-3-methyl-1-butyne

3-N-Chloroacetyl amino-3-methyl-1-butyne (3.19 g or 0.02 M) was dissolved in 35 ml of tetrahydrofuran and 4.09 g (0.022 M) 3-N-O,O-diethyl dithiophosphoric acid was added with cooling below 15° C. With cooling below 25° C., 2.22 g (0.022 M) triethylamine was added to the mixture. The pH was adjusted to 7.5 with additional triethylamine.

The mixture was stirred at ambient temperature for two hours. It was then allowed to stand overnight. After evaporation of the solvent by reduced pressure, the residue was taken up in 75 ml of benzene. It was washed twice with dilute sodium chloride solution. Then it was dried over magnesium sulfate, filtered, and evaporated under reduced pressure, yielding 5.7 g (92% yield) of a liquid product which solidified on standing (m.p. 57°–60° C.). Structure was confirmed by NMR.

Other compounds prepared by this procedure appear in Table I.

TABLE I

Butynylamide Phosphates and Phosphonates Insecticides and Miticides $$HC\equiv C-\underset{\underset{CH_3}{|}}{\overset{\overset{CH_3}{|}}{C}}-NH-\overset{\overset{O}{\|}}{C}-CH_2-S-\overset{\overset{X}{\|}}{P}\underset{R_1}{\overset{R}{<}}$$

| Compound No. | X | R | $R_1$ | Chemical Name | Physical Constant |
|---|---|---|---|---|---|
| 1 | S | $C_2H_5$ | $OC_2H_5$ | 3-N-ethyl,O-ethylphosphonodithioylacetyl-amino-3-methyl-1-butyne | $n_D^{30}$ 1.5353 |

TABLE I-continued

Butynylamide Phosphates and Phosphonates
Insecticides and Miticides $$HC\equiv C-C(O)NH-CH(CH_3)-CH_2-S-P(=X)(R)(R_1)$$

| Compound No. | X | R | $R_1$ | Chemical Name | Physical Constant |
|---|---|---|---|---|---|
| 2 | S | $C_2H_5$ | $OC_3H_7$-i | 3-N-ethyl,O-isopropylphosphonodithioyl-acetylamino-3-methyl-1-butyne | $n_D^{30}$ 1.5275 |
| 3 | S | $C_2H_5$ | $OC_4H_9$-i | 3-N-ethyl,O-isobutylphosphonodithioyl-acetylamino-3-methyl-1-butyne | $n_D^{30}$ 1.5231 |
| 4 | S | $OCH_3$ | $OCH_3$ | 3-N-O,O-dimethylphosphorodithioylacetyl-amino-3-methyl-1-butyne | m.p. 50°–53° C. |
| 5 | S | $OC_2H_5$ | $OC_2H_5$ | 3-N-O,O-diethylphosphorodithioylacetyl-amino-3-methyl-1-butyne | m.p. 57°–60° C. |
| 6 | O | $OC_2H_5$ | $OC_2H_5$ | 3-N-O,O-diethylphosphorothioylacetylamino-3-methyl-1-butyne | waxy solid |
| 7 | S | $OC_3H_7$ | $OC_3H_7$ | 3-N-O,O-di-n-propylphosphorodithioylacetyl-amino-3-methyl-1-butyne | $n_D^{30}$ 1.5143 |
| 8 | S | $OC_3H_7$-i | $OC_3H_7$-i | 3-N-O,O-diisopropylphosphonodithioylacetyl-amino-3-methyl-1-butyne | $n_D^{30}$ 1.5084 |

Insecticidal and Miticidal Evaluation Tests

The term "insect" is used herein broadly to describe not only six-legged winged species of the insecta class, but also wingless arthropods having more than six legs.

Screening was initiated at a maximal concentration level believed to be injurious to the insect population. The initial level should not be understood as representing a maximum at which a viable test for insecticidal activity can be conducted. Concentrations of the test compounds were successively diluted to levels necessary to obtain 50% mortality ($LD_{50}$) of the treated insect population.

Mobile insects, such as houseflies, German cockroaches, and Lygus bugs, were contained for treatment in circular cardboard cages covered with cellophane on the bottom and tulle netting on the top.

The insecticidal and miticidal properties of the compounds of Table I were tested on the following species.

Housefly [*Musca domestica* (Linn.)], (HF)—Contact Residue Assay

Test compounds were diluted in acetone and aliquots were pipetted onto the bottom of 55×15 millimeter (mm) aluminum dishes. One ml of acetone containing 0.02% peanut oil was added to each dish to insure even spreading. After all solvents had evaporated the dishes were placed in cages each containing 25 one to two day old female houseflies. Each cage contained a sugar-water saturated cotton plug for sustenance of the flies.

Mortality rates were recorded after 48 hours. Test levels ranged from 10 μg/25 ♀ houseflies down to that at which approximately 50% mortality occurs.

Black Bean Aphid [*Aphis fabae* (Scop.)]

Black bean aphids were treated to evaluate the effectiveness of the compounds when applied by both (1) direct spraying (BBA), and (2) systemically (BAS).

(1) Nasturtium plants, *Tropaeolum sp.*, approximately five centimeters (cm) high were transplanted into sandy loam soil in three-inch clay pots. Each pot was infested with 25–50 black bean aphids of mixed ages. Twenty-four hours later the pots were sprayed to the point of run-off with 50—50 acetone-water solutions of the test compounds.

Mortality rates were recorded after the infested plants had been held in the greenhouse for three days. Test concentrations ranged from 0.05% down to that at which 50% mortality occurs.

(2) Systemic assay involved diluting the test compounds in acetone and thoroughly mixing aliquots with 500 g portions of dry sandy loam soil. A nasturtium plant was transplanted into each portion of treated soil contained in a pint-sized carton. The plant was infested with 25 aphids of mixed ages.

Mortality rates were recorded 7 days later. Plants which had 100% mortality at 1 part per million (ppm) were reinfested with aphids. The procedure was repeated weekly until all control was lost. Test concentrations ranged from 10 ppm down to that at which approximately 50% mortality occurs.

Green Peach Aphid [*Myzus persicae* (Sulzer)], (GPA)

The insecticidal properties were tested in the same manner as for black bean aphids with the substitution of the nasturtiums by radish plants, *Rhaphanus sativus*.

Green Peach Aphid Systemic [*Myzus persicae* (Sulzer)], (GPS)

The green peach aphid was treated systemically in the same manner as the black bean aphid. Infestation, however, was on radish plants.

German Cockroach [*Blatella germanica* (Linne)], (GR)—Direct Spray Assay

Test compounds were diluted in a 50—50 acetone-water solution. Two cubic centimeters (cc) of the compound solutions were sprayed through a DeVilbiss type EGA hand spray gun into cages each containing 10 one-month-old German cockroach nymphs.

The percent mortality was recorded 7 days later. Test concentrations ranged from 0.1% down to that at which approximately 50% mortality occurs.

Lygus bug [*Lygus hesperus* (Knight)], (LB)—Direct Spray Assay

The species was treated in the same manner as the German cockroach. The cages contained one string bean pod and 10 adult Lygus bugs. The percent mortality was recorded 48 hours later. Test concentrations ranged from 0.05% down to that at which approximately 50% mortality occurs.

Saltmarsh Caterpillar [*Estigmene acrea* (Drury)], (SMC) Leaf Dip Assay

Test compounds were diluted in a 50—50 acetone-water solution. Approximately 1×1.5 inch sections of curly dock (*Rumex crispus*) leaves were immersed in the test solution for 2-3 seconds. After drying on a wire screen, the leaves were placed in petri dishes containing a moistened piece of filter paper. Each dish was infested with 5 second-instar saltmarsh larvae.

Mortality of the larvae was recorded 48 hours later. A piece of synthetic media was added to the dishes containing surviving larvae. The larvae were then observed for 5 additional days for delayed effects of the test compounds. Test concentrations ranged from 0.05% down to that at which approximately 50% mortality occurs.

Cabbage Looper [*Trichoplusia ni* (Hubner)], (CL)

The effectiveness of the compounds was tested in the same manner as for the saltmarsh caterpillar with two exceptions. Cotyledons of hyzini squash, *Calabacita abobrinha*, were substituted for curly dock leaves, and the initial test concentration was 0.1%.

Tobacco Budworm [*Heliothis virescens* (Fabricius)], (TBW)

Tobacco budworms were treated in the same manner as the cabbage looper. Romain lettuce (*Latuca sativa*) leaves provided the substrate.

Two-Spotted Mite [*Tetranychus urticae* (Koch)], (2SM)

Pinto bean plants (*Phaseolus vulgaris*) approximately 10 cm high were transplanted into sandy loam soil in three-inch clay pots. The plants were thoroughly infested with two-spotted mites of mixed ages and sexes. Twenty-four hours after infestation the plants were inverted and dipped for 2-3 seconds in 50-50 acetone-water solutions of the test compounds.

Mortality ratings for both adult mites and nymphs hatching after treatment were taken seven days later. Test concentrations ranged from 0.05% down to that at which 50% mortality occurs.

Southern House Mosquito Larvae (*Culex pipiens quinquefasciatus*), (M)

Ten third-instar larvae were placed in a six ounce wax paper cup containing 100 ml of an aqueous solution of the test compounds at a concentration of 1 ppm. The treated larvae were stored at 70° F. (21.5° C.) and mortality was recorded 48 hours after treatment.

The results of these tests appear in Table II. A less than 50% mortality rate at the initial concentration is indicated by a "greater than" sign (>). An approximate 50% mortality rate is indicated by the initial concentration rate. Other results are the dilutions at which an $LD_{50}$ was achieved.

| KEY TO TABLE II | | |
|---|---|---|
| HF | : | Housefly |
| BBA | : | black bean aphid |
| BAS | : | blAck bean aphid systemic |
| GPA | : | green peach aphid |
| GPS | : | green peach aphid systemic |
| GR | : | German cockroach |
| LB | : | Lygus bug |
| SMC | : | saltmarsh caterpillar |
| CL | : | cabbage looper |
| TBW | : | tobacco budworm |
| 2SM | : | two-spotted mite |
| M | : | mosquito |

TABLE II

Insecticidal and Miticidal Effectiveness Butynlamide Phosphates and Phosphonates $LD_{50}$ VALUES

| Cmpd. No. | HF μg/25 ♀ | BBA % | BAS ppm | GPA % | GPS ppm | GR % | LB % | SMC % | CL % | TBW % | 2SM Adults % | 2SM Eggs % | M ppm |
|---|---|---|---|---|---|---|---|---|---|---|---|---|---|
| Initial Screen Level: | | | | | | | | | | | | | |
|  | 10 | .05 | 10 | .05 | 10 | .10 | .05 | .05 | .1 | .1 | .05 | .05 | 1 |
| 1 | >10 | .0002 | .1 | .001 | 2 | .03 | .009 | >.05 | >.1 | >.1 | .01 | .03 | 1 |
| 2 | >10 | .0001 | .3 | .002 | 1 | .03 | .03 | >.05 | >.1 | >.1 | .005 | .005 | >1 |
| 3 | >10 | .0001 | >10 | .0007 | >10 | .01 | .007 | — | .01 | >.005 | .001 | .03 | .05 |
| 4 | >10 | .001 | 10 | .03 | 3 | .09 | >.05 | >.05 | >.1 | >.1 | >.005 | >.005 | >1 |
| 5 | >10 | .002 | 3 | .005 | 3 | .04 | >.05 | <.01 | >.1 | >.1 | .0008 | .002 | >1 |
| 6 | >10 | .003 | 3 | .05 | >10 | >.1 | >.05 | >.05 | >.1 | >.1 | >.005 | >.005 | 10 |
| 7 | >10 | >.005 | >10 | — | — | — | — | — | — | >.005 | .01 | .03 | >1 |
| 8 | >10 | >.005 | — | — | — | — | — | — | — | >.05 | .05 | >.05 | >1 |

\> = greater than
< = less than
— = not tested

Formulations

The compounds of this invention are generally formulated into a form suitable for convenient application.

It is possible to use a 100% pure compound or highly concentrated liquid for application by atomizing equipment, such as aerial spraying.

Generally, the compounds are formulated with one or more inert carriers or diluents. Liquid compositions, such as emulsions, solutions, suspensions, emulsifiable concentrates and pastes, may additionally contain: surface-active wetting, dispersing, and emulsifying agents; solvents; adhesives; thickeners; binders; and anti-foaming agents.

Compositions generally contain from 5 to 95% active ingredient and preferably contain 10 to 85% active compound.

Wettable powders and pastes are obtained by mixing and grinding an active compound with one or more dispersing agents, such as lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, e.g., butanol, cyclohexane, xylenes, or higher boiling aromatic hydrocarbons. To obtain suspensions or emulsions in water, wetting agents are also added.

Solid formulations include dusts, granules, tablets, powders and the like. Solid carriers or diluents include: ground natural minerals, e.g., kaolins, alumina, calcium carbonate, silica, kieselguhr, clay, etc., ground synthetic minerals, e.g., silicates and alumino-silicates; and ground vegetable products, e.g., bark, cornmeal, sawdust, cellulose powder and the like.

Granules may be manufactured by dissolving an active compound in an organic solvent and applying the mixture by atomization onto an absorptive granuled inert material. Adhesives may be utilized for incorporation of the compounds onto the solid particles.

Formulations may also contain other active pesticidal agents, such as herbicides, fungicides, insecticides, acaricides, nematocides, bactericides, and plant growth regulators.

Multi-purpose compositions may additionally contain soil disinfectants, fumigants, and fertilizers.

Insectidical control may be achieved by direct application of the active compound to the insect. It may be accomplished indirectly by application to insect food sources and habitats.

It should be noted that the active compounds need not be insecticidally active per se to effect insect control. The purposes of this invention are fully served if such compounds are rendered active by external influences, such as light or heat, or by some physiological action which occurs when the compound is ingested into the body of the insect.

Compositions containing one or more of the active compounds described, in an insecticidally effective amount, may be applied to the plant, locus or insect habitat in any conventional manner.

When used in connection with crop or other plant protection, application may be made in a preventive (i.e. before infestation) or eradicative manner (after infestation). Thus, powders and various liquid compositions containing the active compound can be applied by the use of power dusters, boom and hand sprayers and spray dusters, or applied from airplanes as dusts or sprays. When applied in the latter method they may be effective in very low dosages.

Compositions including active compounds may also be applied by addition to irrigation waters supplied to the field to be treated. This method of application permits penetration of the compounds into the soil as the water is absorbed therein.

Compositions applied to the surface of the soil can be distributed below the surface of the soil by conventional means such as discing or mixing operations.

I claim:

1. A method of controlling insects or mites which comprises applying to the insects or mites or the locus thereof an insecticidally or miticidally effective amount of a compound having the formula

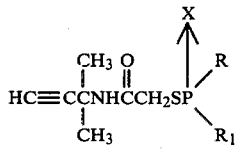

in which
X is selected from the group consisting of sulfur and oxygen;
R is selected from the group consisting of 1-4 carbon alkyl and 1-6 carbon alkoxy; and
$R_1$ is 1-6 carbon alkoxy.

2. A method according to claim 1 in which X is sulfur, R is ethyl, and $R_1$ is alkoxy.

3. A method according to claim 2 in which $R_1$ is ethoxy.

4. A method according to claim 2 in which $R_1$ is isopropyloxy.

5. A method according to claim 2 in which $R_1$ is isobutyloxy.

6. A method according to claim 1 in which X is sulfur, and R and $R_1$ are each alkoxy.

7. A method according to claim 6 in which R and $R_1$ are each methoxy.

8. A method according to claim 6 in which R and $R_1$ are each ethoxy.

9. A method according to claim 1 in which X is oxygen, and R and $R_1$ are each ethoxy.

10. A compound having the formula

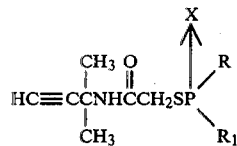

in which
X is selected from the group consisting of sulfur and oxygen;
R is selected from the group consisting of 1-4 carbon alkyl and 1-6 carbon alkoxy; and
$R_1$ is 1-6 carbon alkoxy.

11. A compound according to claim 10 in which X is sulfur, R is ethyl, and $R_1$ is alkoxy.

12. A compound according to claim 11 in which $R_1$ is ethoxy.

13. A compound according to claim 11 in which $R_1$ is isopropyloxy.

14. A compound according to claim 11 in which $R_1$ is isobutyloxy.

15. A compound according to claim 10 in which X is sulfur, and R and $R_1$ are each alkoxy.

16. A compound according to claim 15 in which R and $R_1$ are each methoxy.

17. A compound according to claim 15 in which R and $R_1$ are each ethoxy.

18. A compound according to claim 10 in which X is oxygen, and R and $R_1$ are each ethoxy.

19. An insecticidal or miticidal composition of matter comprising
(a) an insecticidally or miticidally effective amount of a compound having the formula

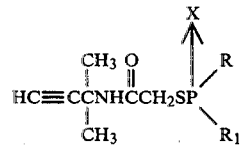

in which
X is selected from the group consisting of sulfur and oxygen;
R is selected from the group consisting of 1-4 carbon alkyl and 1-6 carbon alkoxy; and
$R_1$ is 1-6 carbon alkoxy; and (b) an inert carrier or diluent.

20. A composition according to claim 19 in which X is sulfur, R is ethyl, and $R_1$ is alkoxy.

21. A composition according to claim 20 in which $R_1$ is ethoxy.

22. A composition according to claim 20 in which $R_1$ is isopropyloxy.

23. A composition according to claim 20 in which $R_1$ is isobutyloxy.

24. A composition according to claim 19 in which X is sulfur, and R and $R_1$ are each alkoxy.

25. A composition according to claim 24 in which R and $R_1$ are each methoxy.

26. A composition according to claim 24 in which R and $R_1$ are each ethoxy.

27. A composition according to claim 19 in which X is oxygen and R and $R_1$ are each ethoxy.

* * * * *